United States Patent [19]

Stutz et al.

[11] 4,124,712
[45] Nov. 7, 1978

[54] ERGOT PEPTIDE ALKALOID DERIVATIVES

[75] Inventors: Peter Stütz, Vienna, Austria; Paul Stadler, Biel-Benken, Switzerland

[73] Assignee: Sandoz Ltd., Basel, Switzerland

[21] Appl. No.: 829,206

[22] Filed: Aug. 30, 1977

[30] Foreign Application Priority Data

Sep. 6, 1976 [CH] Switzerland ............... 11286/76
Sep. 6, 1976 [CH] Switzerland ............... 11287/76
Jul. 6, 1977 [CH] Switzerland ............... 8335/77

[51] Int. Cl.² ............... A61K 31/495; C07D 413/14
[52] U.S. Cl. ............... 424/250; 544/346
[58] Field of Search ............... 260/250 BC, 268 PE, 260/268 TR; 424/250

[56] References Cited

U.S. PATENT DOCUMENTS

| | | | |
|---|---|---|---|
| 3,084,168 | 4/1963 | Frey | 260/268 PE |
| 3,227,719 | 1/1966 | Hofmann | 260/268 PE |
| 3,336,311 | 8/1967 | Hofmann | 260/268 PE |

FOREIGN PATENT DOCUMENTS 1,011,113  11/1965  United Kingdom ............... 260/250 BC

*Primary Examiner*—Paul M. Coughlan, Jr.
*Assistant Examiner*—James H. Turnipseed
*Attorney, Agent, or Firm*—Gerald D. Sharkin; Robert S. Honor; Thomas O. McGovern

[57] ABSTRACT

Compounds of formula I,

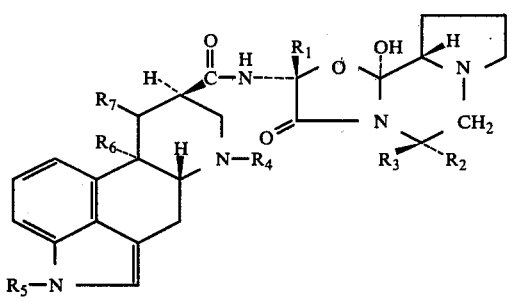

wherein
$R_1$ is alkyl of 1 to 4 carbon atoms,
$R_2$ is hydrogen, alkyl of 1 to 4 carbon atoms or benzyl,
$R_3$ and $R_5$ are, independently, hydrogen or methyl,
$R_4$ is hydrogen or alkyl of 1 to 4 carbon atoms, and
$R_6$ and $R_7$ together form a single bond, or
$R_6$ and $R_7$ are each hydrogen,
$R_6$ is methoxy, and
$R_7$ is hydrogen, are useful in the treatment of hypertension, angina pectoris, depressions, neuroses and psychoses.

24 Claims, No Drawings

ERGOT PEPTIDE ALKALOID DERIVATIVES

IMPROVEMENTS IN OR RELATING TO ORGANIC COMPOUNDS

The present invention relates to ergot peptide alkaloid derivatives.

The present invention provides compounds of formula I,

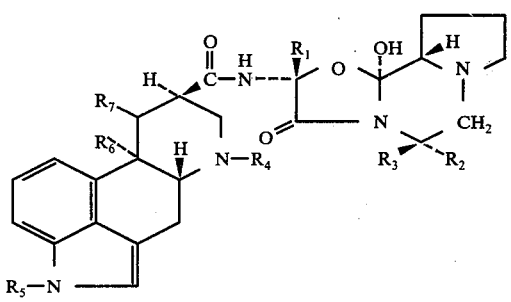

wherein
- $R_1$ is alkyl of 1 to 4 carbon atoms,
- $R_2$ is hydrogen, alkyl of 1 to 4 carbon atoms or benzyl,
- $R_3$ and $R_5$ are, independently, hydrogen or methyl,
- $R_4$ is hydrogen or alkyl of 1 to 4 carbon atoms, and
- $R_6$ and $R_7$ together form a single bond, or
- $R_6$ and $R_7$ are each hydrogen, or
- $R_6$ is methoxy and $R_7$ is hydrogen.

In formula I, $R_1$ is for example methyl, ethyl or iso-propyl. $R_2$ is conveniently n- or iso-propyl, n-, iso- or sec.-butyl or benzyl. $R_3$ and $R_5$ conveniently are both hydrogen. $R_4$ is conveniently methyl or iso-propyl. $R_6$ and $R_7$ are preferably each hydrogen.

The present invention also provides a process for the production of a compound of formula I, which comprises
a. reducing the 6' carbonyl group in a compound of formula II,

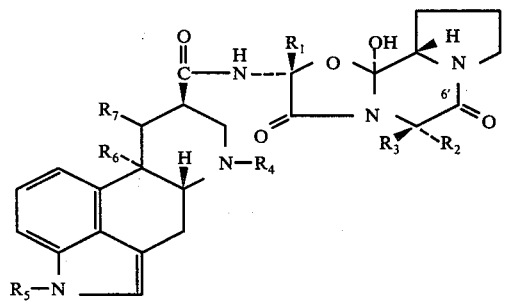

wherein $R_1$ to $R_7$ are as defined above, or
b. condensing an acid addition salt of a compound of formula III,

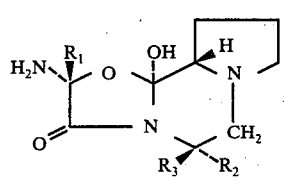

wherein $R_1$ to $R_3$ are as defined above, with a reactive acid derivative of a compound of formula IV,

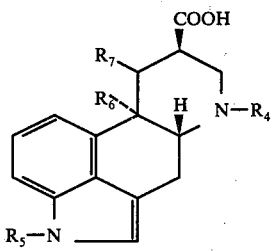

wherein $R_4$ to $R_7$ are as defined above.

Process a) may be effected in one step process if desired, using reactive borane, e.g. diborane. The process may be effected in conventional manner for diborane reductions under mild conditions. Conveniently 5 to 15 moles of reactive borane are used per mole of a compound of formula II. Tetrahydrofuran, diethyl ether or methylene chloride may be used as solvent. Suitable reaction temperatures may be from $-20°$ to $20°$ C.

Process b) may be effected in conventional manner for condensations to produce analogous ergot cyclic peptide alkaloids.

A suitable acid addition salt of a compound of formula III is the 2,5-naphthalene-disulphonic acid salt.

Suitable reactive acid derivatives of a compound of formula IV include the acid chloride, the acid azide, and the mixed anhydride with sulphuric or trifluoroacetic acid. It is preferred to use the addition product of a compound of formula IV with dimethyl formamide or acetamide and thionyl chloride, phosgene or oxalyl chloride. Preferably triethylamine or pyridine is present during the reaction. Suitable solvents include chloroform, methylene chloride, dimethyl formamide and acetonitrile.

Suitable reaction temperatures are from $-30°$ to $+20°$ C.

The starting materials are known or may be produced in conventional manner from known compounds. Thus a compound of formula III may be prepared in known manner for the preparation of an aminocyclol from a compound of formula V;

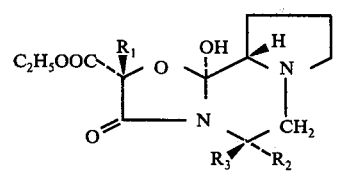

wherein $R_1$ to $R_3$ are as defined above. For example the corresponding acid may first be formed and then converted via the acid chloride into the corresponding acid amide, which in turn is converted into the amine.

A compound of formula V may be produced by reacting a compound of formula VI,

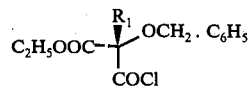

wherein $R_1$ is as defined above, with a compound of formula VII,

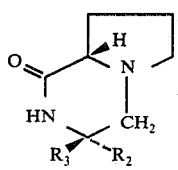

VII wherein $R_2$ and $R_3$ are as defined above, and hydrogenating the resultant product.

A compound of formula VII may be produced by reducing a compound of formula VIII,

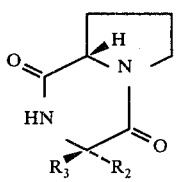

VIII wherein $R_2$ and $R_3$ are as defined above, with lithium aluminium hydride.

Free base forms of the compounds of formula I may be converted into acid addition salt forms in conventional manner and vice versa. Suitable acids for salt formation include hydrochloric and methane-sulphonic acids.

In the following Examples all temperatures are in degrees Centigrade and are uncorrected.

EXAMPLE 1

6'-desoxo-9,10-dihydro-β-ergocryptine

[process a)]

1.15 g of 9,10-dihydro-β-ergocryptine (2 mmols) are suspended and stirred at 0° in 25 ml of absolute tetrahydrofuran and then a freshly prepared solution of 20 mmols reactive borane (e.g. from $NaBH_4$ and boron trifluoride etherate) in 35 ml of absolute tetrahydrofuran is added dropwise. After stirring for 4 hours at 0° the solution is cooled. The reaction mixture is carefully treated with 9 ml of 6N-hydrochloric acid, and then stirred for another 30 minutes at +60°, cooled, made alkaline with 30% sodium hydroxide, and then thoroughly extracted with methylene chloride. The methylene chloride extracts are chromatographed on aluminia (activity II-III) to yield the title compound in free base form which is recrystallized from methylene chloride/ether. M.Pt. 159°-160°; $[\alpha]_D^{20} = -4°$ ($c = 0.5$ DMF).

The title compound may also be prepared according to the process of Example 2.

EXAMPLE 2

1-methyl-6'-desoxo-9,10-dihydroergocristine [process b)]

A solution of 1.14 ml (17.14 mmols) of oxalyl chloride in 15 ml of absolute acetonitrile is added dropwise to 150 ml of absolute dimethyl formamide at −15°. 4.87 g (17.14 mmols) of dry 1-methyl-9,10-dihydrolysergic acid are then added, and a grey deposit precipitates from the reaction mixture. After stirring for 30 minutes at 0°, the mixture is cooled and treated with 37.5 ml of absolute pyridine, and then 5.14 g of (2R,5S,10aS,10bS)-2-amino-2-isopropyl-3-oxo-5-benzyl-10b-hydroxy-perhydrooxazolo[3,2-a]-pyrrolo[2,1-c]pyrazine.2,5-naphthalene-disulphonic acid (about 8.5 mmols) are added. The mixture is stirred vigorously for 2 hours, and then the temperature is allowed to increase slowly from −10° to 0°. The mixture is then cooled again and diluted with 40 ml of citratebuffer (pH = 4), and then made alkaline with 2N soda solution. After extraction with chloroform containing a small amount of ethanol, the extract is dried and evaporated. The crude product is chromatographed on silicagel, to give the title compound in free base form on elution with 4% methanol in methylene chloride, which is recrystallised from acetone.

M.Pt. 183°–185°; $[\alpha]_D^{20} = -77°$ ($c = 1$, pyridine).

The title compound may also be prepared by the process of Example 1.

The 2-amino-2-isopropyl-3-oxo-5-benzyl-10b-hydroxyperhydrooxazolo[3,2-a]pyrrolo[2,1-c]pyrazine.2,5-naphthalene-disulphonic acid is obtained as follows:

A. (2S,7AS)-2-BENZYL-PERHYDRO-8-OXO-PYRROLO[2,1-C]PYRAZINE 36.4 g (960 mmols) of lithium aluminium hydride are suspended in 1.3 liters of absolute tetrahydrofuran in a nitrogen atmosphere, and a solution of 117.2 g (480 mmols) of L-Phe-L-Pro-lactam in 1.4 liters of absolute tetrahydrofuran is added dropwise over 45 minutes. After stirring for 18 hours at −10°, the reaction mixture is diluted carefully at this temperature with 350 ml of ethyl acetate and then 350 ml of water. The resultant mixture is filtered. Repeated extraction of the filter cake with boiling methylene chloride is effected to obtain more product. The combined organic phases and filtrate are dried with sodium sulphate and evaporated. The pure title compound in free base form crystallises directly from methylene chloride/ether in bright beige crystals; M.Pt. of 135°–140°; $[\alpha]_D^{20} = -3.5°$ ($c = 1$ in ethanol).

B. (2R,5S,10AS,10BS)-2-CARBETHOXY-2-ISOPROPYL-3-OXO-5-BENZYL-10B-HYDROXY-PERHYDRO-OXAZOLO[3,2-A]PYRROLO[2,1-C]PYRAZINE (bi) 47.8 g (207 mmols) of (2S,7aS)-2-benzyl-perhydro-8-oxo-pyrrolo[2,1-c]pyrazine in 160 ml of absolute dioxane are treated with 74.4 g (249 mmols) of S-(+)-isopropyl-benzyloxy-malonic acid mono-ethyl ester mono-acid chloride and 34.9 g (270 mmols) of N-ethyl-diisopropylamine. The mixture is stirred for 1 hour at +70°. After dilution with 1 liter of ether, the mixture is shaken twice with saturated sodium bicarbonate solution and dried over sodium sulphate. After evaporation of the solvent, 138 g of a brownish oil containing (2S,7aS)-(2'S-2'-benzyloxy-2'-isopropyl-O-ethyl-malononyl)-2-benzyl-perhydro-8-oxo-pyrrolo[2,1-c]-pyrazine are obtained.

(bii) This oil is dissolved in 1.5 liters of ethanol and is hydrogenated at 60° after addition of 60 g of palladium-active carbon (10% w/w Pd), wherein, after 14 hours, about 6.5 liters of hydrogen are absorbed. After filtration and evaporation of the filtrate, the title compound is recrystallized from isopropyl ether, as yellowish prisms with a M.Pt. of 99°–100°; $[\alpha]_D^{20} = -57.7°$ ($c = 0.65$ in $CHCl_3$).

C. (2R,5S,10AS,10BS)-2-CARBOXY-2-ISOPROPYL-3-OXO-5-BENZYL-10B-HYDROXY-PERHYDRO-OXAZOLO[3,2-A]PYRROLO[2,1-C]PYRAZINE 39.3 g (97.8 mmols) of (2R,5S,10AS,10BS)-2-carbethoxy-2-isopropyl-3-oxo-5-benzyl-10b-hydroxy-perhydro-oxazolo[3,2-a]pyrrolo[2,1-c]pyrazine are dissolved in 245 ml of methanol and 245 ml of 2 N sodium hydroxide. The mixture is stirred for 3 hours at room temperature, adjusted at 0° to a pH of 4.5 with 2 N hydrochloric acid, and then extracted repeatedly with ethyl acetate. After drying the organic extract and evaporating the solvent at below +30°, the title compound crystallises after dilution with ether. M.Pt. 126°–128° (decomp). After drying for 5 hours at 30° in a high vacuum, the crystals contain ~ ½ mol water per mole of title compound.

D. (2R,5S,10AS,10BS)-2-AMINO-2-ISOPROPYL-3-OXO-5-BENZYL-10B-HYDROXY-PERHYDRO-OXAZOLO[3,2-A]PYRROLO[2,1-C]PYRAZINE.2,5-NAPHTHALENE DISULPHONIC ACID (di) A solution of 3.84 ml (45 mmols) of oxalyl chloride in 15 ml of absolute acetonitrile is added in drops over 10 minutes to a stirred mixture of 4.33 ml (56.3 mmols) of absolute dimethyl formamide and 30 ml of absolute acetonitrile which is cooled to −15°. The mixture is stirred for a further 10 minutes. After dilution of the mixture with 45 ml of absolute ether, 11.25 g (30 mmols) of (2R,5S,10AS,10BS)-2-carboxy-2-isopropyl-3-oxo-5-benzyl-10b-hydroxy-perhydro-oxazolo[3,2-a]pyrrolo[2,1-c]pyrazine.½ H₂O are quickly added. A clear solution is produced, which is stirred for another 10 minutes at −10° thereby producing the acid chloride.

(dii) A solution of 20 g of sodium azide in 100 ml of water, diluted with 300 ml of methylene chloride, is added to the acid chloride solution and the 2-phase mixture is shaken vigorously for 4 minutes. Then, 150 ml of ice-cold, saturated sodium bicarbonate solution are added. The organic phase is separated and dried well over sodium sulphate. After evaporation of the solvent at below 30°, a solution of 7.78 g (27 mmols) of 2,5-naphthalene disulphonic acid in 200 ml of dimethoxyethane and 20 ml of acetonitrile is added. The mixture is then slowly concentrated in a vacuum. After dilution of the mixture with absolute ether, the acid azide is isolated as the 2,5-naphthalene disulphonate salt.

(diii) 6.35 g (~ 9mmols) of the salt are heated for 1 hour to 80° in the presence of 120 ml of dimethoxyethane which contains 0.166 ml of water. The title compound is obtained with constant scraping, as a brownish, semi-crystalline powder, which may be used directly after cooling, filtering and drying at room temperature in a high vacuum.

The following compounds of formula I may also be obtained in analogous manner to that described in Example 1 or 2.

EXAMPLE 3

6′-desoxo-9,10-dihydro-α-ergocryptine

M.Pt. 182°–185°; $[\alpha]_D^{20} = +14°$ ($c = 0.3$ in dimethyl formamide).

EXAMPLE 4

6′-desoxo-9,10-dihydroergocornine

M.Pt. 166°–167° (decomp); $[\alpha]_D^{20} = -18.5°$ ($c = 0.66$ in dimethyl formamide).

EXAMPLE 5

6′-desoxo-9,10-dihydro-β-ergosine

M.Pt. 194°–196° (sintering from 185°); $[\alpha]_D^{20} = -18°$ ($c = 0.3$ in dimethyl formamide).

EXAMPLE 6

6-nor-6-isopropyl-6′-desoxo-9,10-dihydroergotamine

M.Pt. 186°–190°; $[\alpha]_D^{20} = -63°$ ($c = 0.3$ in dimethyl formamide).

EXAMPLE 7

6′-desoxo-ergotamine

M.Pt. 176°–180°; $[\alpha]_D^{20} = +17°$ ($c = 0.35$ in dimethyl formamide).

EXAMPLE 8

6′-desoxo-ergocristine

EXAMPLE 9

6′-desoxo-β-ergocryptine

EXAMPLE 10

6′-desoxo-α-ergocryptine

EXAMPLE 11

6′-desoxo-9,10-dihydroergocristine

M.Pt. 208°–209° (decomp.); $[\alpha]_D^{20} = -75°$ ($c = 0.8$, pyridine).

EXAMPLE 12

6′-desoxo-9,10-dihydroergotamine

M.Pt. 165°–168° (decomp.); $[\alpha]_D^{20} = -78°$ ($c = 1$, pyridine).

In analogous manner to that disclosed in Example 2, the following compound of formula I may be prepared, wherein:

(a) $R_1$ is n-butyl, $R_2$ is hydrogen, $R_3$ is methyl, $R_4$ is hydrogen, $R_5$ is methyl and $R_6$ and $R_7$ are each hydrogen.

(b) $R_1$ is n-butyl, $R_2$ is hydrogen, $R_3$ is methyl, $R_4$ is hydrogen, $R_5$ is methyl, $R_6$ is methoxy and $R_7$ is hydrogen.

The compounds of formula I are useful because they possess pharmacological activity in animals. In particular, the compounds of formula I are useful as coronary therapeutic agents e.g. for the treatment of angina pectoris, as indicated by a coronary dilation and vasodilation in the "open chest cat" test at an effective dose of from about 0.03 to about 1 mg/kg i.v.

The compounds are also useful as anti-hypertensives as indicated by a blood pressure lowering in the above-mentioned open chest cat test.

The compounds are also useful as anti-depressants as indicated by standard tests, e.g. in the tetrabenazine-induced catalepsy antagonism test in rats at doses of from about 50 to about 100 mg/kg i.p.

The compounds are also useful as neuroleptics, as indicated in standard tests in rats, e.g. in rats at doses of from about 50 to 100 mg/kg i.p.

For all the above mentioned uses the dosage will, of course, vary depending on the compound employed, mode of administration and therapy desired. However, in general, satisfactory results are obtained when administered at a daily dosage of from 0.03 mg to about 100 mg per kg animal body weight, conveniently given in divided doses 2 to 4 times a day or in sustained release form. For the larger mammal, the total daily dosage is in the range from about 10 to about 300 mg, and dosage forms suitable for oral administration comprise from about 2 mg to about 150 mg of the compounds admixed with a solid or liquid pharmaceutical carrier or diluent.

The Example 1 compound is the preferred compound and shows notable coronary therapeutic and hypotensive properties in the above tests.

The compounds may be administered in pharmaceutically acceptable acid addition salt form. Such salt forms have the same order of activity as the free base forms. The present invention provides a pharmaceutical composition comprising a compound of formula I as defined above in association with a pharmaceutical carrier or diluent. Such compositions may be formulated in conventional manner so as to be for example a solution or a tablet.

In a group of compounds $R_1$ is methyl, ethyl or isopropyl, $R_2$ is H, $CH_3$, $C_2H_5$, n- or iso-$C_3H_7$, n-, iso, or sec-butyl or benzyl, $R_4$ is H, $CH_3$, $C_2H_5$, n- or iso-$C_3H_7$ or n-, iso- or sec-butyl, and either $R_6$ and $R_7$ are each hydrogen or together form a bond.

In one group of compounds $R_6$ and $R_7$ together form a single bond. In a second group of compounds $R_6$ is hydrogen. In a third group of compounds $R_6$ is methoxy.

We claim:
1. A compound of formula I,

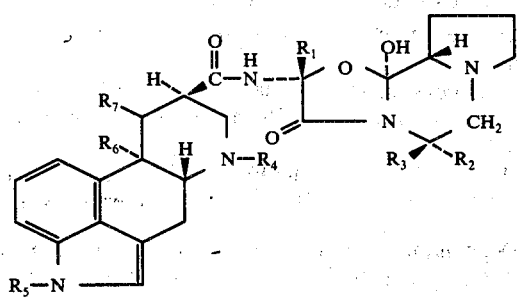

I wherein
$R_1$ is alkyl of 1 to 4 carbon atoms,
$R_2$ is hydrogen, alkyl of 1 to 4 carbon atoms or benzyl,
$R_3$ and $R_5$ are, independently, hydrogen or methyl,
$R_4$ is hydrogen or alkyl of 1 to 4 carbon atoms, and
$R_6$ and $R_7$ together form a single bond, or
$R_6$ and $R_7$ are each hydrogen,
$R_6$ is methoxy, and $R_7$ is hydrogen,
in free base form or in pharmaceutically acceptable acid addition salt form.

2. A compound of claim 1, wherein $R_1$ is methyl, ethyl or isopropyl, $R_2$ is H, $CH_3$, $C_2H_5$, n- or iso-$C_3H_7$ or n-, iso- or sec-butyl, or benzyl, and $R_4$ is H, $CH_3$, $C_2H_5$, n- or iso-$C_3H_7$ or n-, iso- or sec-butyl, and either $R_6$ and $R_7$ are each hydrogen, or together form a bond.

3. A compound of claim 1, which is 6-desoxo-9,10-dihydro-β-ergocryptine.

4. A compound of claim 1, which is 1-methyl-6'-desoxo-9,10-dihyroergocristine.

5. A compound of claim 1, which is 6'-desoxo-9,10-dihydro-α-ergocryptine.

6. A compound of claim 1, which is 6'-desoxo-9,10-dihydroergocornine.

7. A compound of claim 1, which is 6'-desoxo-9,10-dihydro-β-ergosine.

8. A compound of claim 1, which is 6-nor-6-isopropyl-6'-desoxo-9,10-dihydroergotamine.

9. A compound of claim 1, which is 6'-desoxoergotamine.

10. A compound of claim 1, which is 6'-desoxoergocristine.

11. A compound of claim 1, which is 6'-desoxo-9,10-dihydroergocristine.

12. A compound of claim 1, which is 6'-desoxo-9,10-dihydroergotamine.

13. A compound of claim 1, which is 6'-desoxo-β-ergocryptine.

14. A compound of claim 1, which is 6'-desoxo-α-ergocryptine.

15. A compound of any one of claim 1 in free base form.

16. A compound of any one of claim 1 in acid addition salt form.

17. A pharmaceutical composition useful in treating angina pectoris comprising a therapeutically effective amount of a compound of claim 1 in association with a pharmaceutical carrier or diluent.

18. A pharmaceutical composition according to claim 17 in which the compound is 6'-desoxo-9,10-dihydro-β-ergocryptine.

19. A method of treating angina pectoris, in an animal which comprises administering a therapeutically effective amount of a compound of claim 1 to an animal in need of said treatment.

20. A method according to claim 19 in which 10 to 300 milligrams of the compound are administered daily.

21. A method according to claim 19 in which 2 to 150 milligrams of the compound are administered per unit dose.

22. A method according to claim 19 in which the compound is 6'-desoxo-9,10-dihydro-β-ergocryptine.

23. A method according to claim 20 in which the compound is 6'-desoxo-9,10-dihydro-β-ergocryptine.

24. A method according to claim 21 in which the compound is 6'-desoxo-9,10-dihydro-β-ergocryptine.

* * * * *